US006214578B1

(12) United States Patent
Ueki et al.

(10) Patent No.: US 6,214,578 B1
(45) Date of Patent: Apr. 10, 2001

(54) METHOD FOR THE EXPRESSING FOREIGN GENES AND VECTORS THEREFOR

(75) Inventors: Jun Ueki; Shozo Ohta, both of Shizuoka; Shinji Morioka, Tokyo; Yoshiki Kuraya, Shizuoka, all of (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 09/011,526

(22) PCT Filed: Jun. 12, 1997

(86) PCT No.: PCT/JP97/02030

§ 371 Date: Feb. 12, 1998

§ 102(e) Date: Feb. 12, 1998

(87) PCT Pub. No.: WO97/47755

PCT Pub. Date: Dec. 18, 1997

(30) Foreign Application Priority Data

Jun. 12, 1996 (JP) ...................................... 8-172922

(51) Int. Cl.[7] .............................. C12N 15/82; C12N 5/14; C12N 15/11
(52) U.S. Cl. ..................... 435/69.1; 435/468; 435/320.1; 536/23.1; 536/24.1
(58) Field of Search .................................. 435/69.1, 468, 435/320.1; 536/23.1, 24.1

(56) References Cited

U.S. PATENT DOCUMENTS

| 5,614,399 | 3/1997 | Quail et al. . |
| 5,747,327 | 5/1998 | Ueki et al. . |

FOREIGN PATENT DOCUMENTS

| 0 823477A1 | 2/1998 | (EP) . |
| 3-103182 | 4/1991 | (JP) . |

OTHER PUBLICATIONS

Luehrsen et al. Intron enhancement of gene expression ang the splicing efficiency of introns in maize cells. Mol. Gen. Genet. vol. 225 pp. 81–93, 1991.*
Mascarenhas et al. Intron–mediated enhancement of heterologous gene expression in maize. Plant Molecular Biology vol. 15 pp. 913–920, 1990.*
V. Vasil et al., *Plant Physiol.*, 81, 1575–1579 (1989).
A. Tanaka et al., *Nucleic Acids Research*, vol. 18, No 23.
D. Mascarenhas et al., *Plant Molecular Biology*, 15:913–920 (1990).
D. McElroy et al., *the Plant Cell*, vol. 2, 163–171 (Feb. 1990).
K. Luehrsen et al., *Mol. Gen. Genet.*, 225:81–93 (1991).
C. Curie et al., *Nucleic Acids Research*, vol. 19, No. 6.
A. H. Christensen et al., *Plant Molecular Biology*, 18:675–689 (1992).
J. Callis et al., *Genes & Development*, 1:118–1200 (1987).

* cited by examiner

*Primary Examiner*—John S. Brusca
(74) *Attorney, Agent, or Firm*—Birch, Stewart, Kolasch & Birch, LLP

(57) ABSTRACT

A method for expressing a foreign gene, by which the foreign genes can be expressed more strongly than by the conventional methods, as well as a recombinant vector therefor, is disclosed. In the method for expressing a foreign gene according to the present invention, the foreign gene is inserted into a site downstream of a promoter and the foreign gene is expressed in a cell, wherein a plurality of intron-originated DNA fragments which are the same or different and are capable of promoting expression of foreign genes are inserted into one or more sites upstream of the foreign gene, and said foreign gene is expressed.

27 Claims, No Drawings

METHOD FOR THE EXPRESSING FOREIGN GENES AND VECTORS THEREFOR

This application is the national phase under 35 U.S.C. §371 of PCT International Application No. PCT/JP 97/02030 which has an International filing date of Jun. 12, 1997 which designated the United States of America, the entire contents of which are hereby incorporated by reference.

TECHNICAL FIELD

The present invention relates to a method for expressing a foreign gene and a vector therefor. More particularly, the present invention relates to a method for expressing a foreign gene in genetic engineering processes, by which expression of the foreign gene is more strongly promoted than the conventional methods, and to a vector therefor.

BACKGROUND ART

Promotion of expression of foreign genes is one of the most required techniques in genetic engineering processes, especially when the genetic engineering processes are applied to plants.

As one of such methods, it is known to insert an intron-originated DNA fragment into a site upstream of the foreign gene. For example, Japanese Laid-open Patent Application (Kokai) No. 3-103182 discloses that expression of a foreign gene is promoted by inserting an intron-originated DNA fragment of castor-oil plant catalase gene (CAT-1) into a site upstream of the foreign gene, and expressing the foreign gene. Similar phenomena have been reported for various intron-originated DNA fragments.

Although introns have been utilized for the purpose of promoting expression of foreign genes, use of a plurality of introns is not popular, and advantageous effect thereof has not been recognized. For example, although the first intron and the 6th intron of maize alcohol dehydrogenase gene individually promote gene expression, if these introns are ligated, the effect is less than in the case where the 6th intron alone is used (Mascarenhas et al. Plant Mol. Biol., 15, 913–920(1990)). Similarly, in cases where two maize actin third introns are ligated, the effect is less than the case where only one intron is used (Luehrsen et al., Mol. Gen. Genet., 225, 81–93 (1991)).

Although the known methods in which an intron-originated DNA fragment is inserted are effective, the expression-promoting effects are often insufficient. Thus, a method by which gene expression is more strongly promoted is desired.

DISCLOSURE OF THE INVENTION

Accordingly, an object of the present invention is to provide a method for expressing foreign genes by which the foreign genes are more strongly expressed than by the known methods, and to provide recombinant vectors therefor.

The present inventors intensively studied to discover that expression of foreign genes is much more promoted by inserting into one or more sites upstream of the foreign gene a plurality of intron-originated DNA fragments which are the same or different and are capable of promoting expression of foreign genes when inserted into a site upstream of the foreign gene, than in the known methods in which a single intron-originated DNA fragment is inserted, thereby completing the present invention.

That is, the present invention provides a method for expressing a foreign gene comprising inserting said foreign gene into a site downstream of a promoter and expressing said foreign gene in a cell, characterized in that a plurality of intron-originated DNA fragments which are the same or different and are capable of promoting expression of foreign genes are inserted into one or more sites upstream of said foreign gene and said foreign gene is expressed.

The present invention also provides a recombinant vector comprising a promoter, a foreign gene inserted into a site downstream of said promoter, and a plurality of intron-originated DNA fragments which are the same or different and are capable of promoting expression of foreign genes, which are inserted into one or more sites upstream of said foreign gene.

The present inventors discovered that even if a single intron sequence of maize ubiquitin gene, which has a nucleotide sequence shown in SEQ ID NO:3 in the SEQUENCE LISTING, is inserted into a site upstream of a foreign gene, expression of the foreign gene is promoted, thereby completing the second invention of the present application.

That is, the present invention also provides a method for expressing a foreign gene comprising inserting said foreign gene into a site downstream of a promoter, and expressing said foreign gene in a cell, characterized in that the sequence shown in SEQ ID NO: 3 in the SEQUENCE LISTING or a functional variant thereof is inserted into a site upstream of said foreign gene and said foreign gene is expressed.

By the present invention, methods for expressing foreign genes by which expression of the foreign genes are much more strongly promoted than in the known methods, as well as recombinant vectors therefor, were provided. By the present invention, since expression of foreign genes introduced by genetic engineering processes is promoted, it is expected that the present invention will greatly contribute to the field of genetic engineering.

BEST MODE FOR CARRYING OUT THE INVENTION

The method of the present invention is characterized by inserting two or more intron-originated DNA fragments capable of promoting expression of foreign genes into one or more sites upstream of a foreign gene to be expressed, so as to promote expression of the foreign gene.

Here, the term "intron-originated DNA fragment having an effect to promote expression of foreign genes" means a DNA fragment originated from an intron, which is capable of promoting expression of foreign genes to a detectable degree when compared with the case wherein the foreign gene is expressed without inserting the intron-originated DNA fragment. Various such intron-originated DNA fragments per se are known. Examples of such intron-originated DNA fragments include the first intron of catalase gene (CAT-1) of castor-oil plant (Japanese Laid-open Patent Application (Kokai) No. 3-103182; Tanaka et al. Nucleic Acids Res. 18, 6767–6770(1990)); the intron of maize UDP-glucose:flavonol glycosyltransferase (Callis et al., Genes & Develop. 1, 1183–1200 (1987)); the first intron of maize alcohol dehydrogenase-1 (Callis et al., Genes & Develop. 1, 1183–1200 (1987)); the second and the sixth intron of maize alcohol dehydrogenase-1 (Mascarenhas et al., Plant Mol. Biol. 15, 913–920(1990)); the first intron of maize shrunken-1 (Vasil et al., Plant Physiol. 91, 1575–1579 (1989)); the first intron of translation elongation factor EF-1α of *Arabidopsis thaliana*); and the first intron of rice actin (McElroy et al. Plant Cell 2, 163–171(1990)). It should be noted, however, the intron-originated DNA fragments which may be employed in the present invention are not restricted thereto and any intron-originated DNA fragments which can promote expression of foreign genes downstream thereof may be employed.

The present inventors previously discovered introns of rice PLD gene by comparing the nucleotide sequences of the cDNA and the genomic DNA of rice phospholipase D (PLD) gene, discovered that one of these introns prominently promotes expression of genes downstream thereof, and filed a patent application directed thereto (PCT/JP96/00812). The nucleotide sequence of this intron is shown in SEQ ID NO:1 in the SEQUENCE LISTING. In the present invention, this intron-originated DNA fragment shown in SEQ ID NO:1 may be employed. Further, the intron sequence of castor-oil plant catalase gene, shown in SEQ ID NO:2 in the SEQUENCE LISTING and the intron sequence shown in maize ubiquitin gene, which has a nucleotide sequence shown in SEQ ID NO:3, may also preferably be employed.

It is well-known in the art that there are cases wherein the physiological activity of a physiologically active DNA sequence is retained even if one or more nucleotides are added, inserted, deleted or substituted. In the present invention, DNA fragments resulting from such a modification of the above-described known intron-originated DNA fragments or the sequence shown in SEQ ID NO:1, which promote expression of the gene downstream thereof, are included in the term "intron-originated DNA fragments" as used herein. That is, DNA fragments which have the same nucleotide sequences as the above-mentioned known intron-originated DNA fragments or the intron-originated DNA fragment having the nucleotide sequence shown in SEQ ID NO:1 except that one or more nucleotides are added, deleted or substituted, which promote expression of a gene downstream thereof are also included in the "intron-originated DNA fragments" in the present invention. Here, such a modified intron-originated DNA fragment preferably has a homology of not less than 70%, more preferably not less than 90% to the original intron-originated DNA fragment. Similarly, the term "functional variant" recited in the claims means the DNA fragment which has the same nucleotide sequence as the original sequence except that one or more nucleotides are added, deleted or substituted, which promotes expression of a gene downstream thereof, and which preferably has a homology of not less than 70%, more preferably not less than 90% to the original sequence. For example, the term "functional variant of the sequence shown in SEQ ID NO:1" means the DNA fragment having the same nucleotide sequence as shown in SEQ ID NO:1 except that one or more nucleotides are added, deleted or substituted, which promotes expression of a gene downstream thereof, and which preferably has a homology of not less than 70%, more preferably not less than 90% to the original sequence.

Each of the above-described DNA fragments may easily be prepared by the conventional PCR method since the nucleotide sequence and the original source thereof are known. Further, those having sizes of not longer than about 200 bp may be chemically synthesized. The above-mentioned modified intron-originated DNA fragments may easily be prepared by the site-specific mutagenesis method or by chemical synthesis.

In the method of the present invention, a plurality of the above-mentioned intron-originated DNA fragments are inserted into one or more upstream sites of the foreign gene to be expressed, that is, one or more upstream sites of the transcription region, more preferably into the 5'-end of the transcription region. The intron-originated DNA fragments may preferably be inserted between the promoter and the foreign gene. The intron-originated DNA fragments may be inserted into a site immediately upstream of the foreign gene to be expressed, or another sequence may exist between the intron-originated DNA fragments and the foreign gene. The length of this intervening sequence is not restricted and usually 0 to 1000 bp. The promoter and the intron-originated DNA fragments may be directed connected or another sequence may exist therebetween. The length of this intervening sequence is not restricted and usually 0 to 1000 bp.

In the method of the present invention, a plurality of, preferably 2 to 5, more preferably 2 or 3 of the above-described intron-originated DNA fragments are inserted. The intron-originated DNA fragments to be inserted may have the same or different nucleotide sequence. The plurality of the intron-originated DNA fragments may be directly connected or another sequence may exist therebetween. The length of this intervening sequence is not restricted and usually 0 to 1000 bp.

As the promoter, any promoter which can express the foreign gene located downstream thereof may be employed. A preferred example of the promoter is the 35S promoter, although the promoter is not restricted thereto.

The present invention also provides a recombinant vector to which the above-described method of the present invention is applied. That is, the present invention provides a recombinant vector comprising a promoter, a foreign gene inserted into a site downstream of the promoter, and a plurality of intron-originated DNA fragments which are the same or different and are capable of promoting expression of foreign genes, which are inserted into one or more sites upstream of the foreign gene. Such a vector may be obtained by inserting the above-described plurality of intron-originated DNA fragments and the foreign gene into an appropriate expression vector. The insertion may easily be carried out by using appropriate restriction enzymes and, if necessary, linkers because the nucleotide sequence of the cloning site of the expression vector is known.

Various such expression vectors are known in the art and are commercially available. These expression vectors comprise at least a replication origin for replication in the host cell, a promoter, a cloning site giving restriction sites for inserting a foreign gene and a selection marker such as a drug resistance marker. They usually comprise a terminator for stably terminating transcription and an SD sequence in cases where the host cell is a bacterial cell. In the method of the present invention, any of these known expression vectors may be employed.

The present inventors discovered that even if a single intron sequence of maize ubiquitin gene, which has a nucleotide sequence shown in SEQ ID NO:3 in the SEQUENCE LISTING, is inserted in a foreign gene, expression of the foreign gene is promoted. Thus, the cases where only a single sequence shown in SEQ ID NO:3 or a functional variant thereof is inserted in place of the above-described plurality of intron-originated DNA fragments are also included in the scope of the present invention. However, even in cases where the sequence shown in SEQ ID NO:3 is employed, the effect is higher when a plurality of the sequences are inserted, and the effect is especially high when the sequence shown in SEQ ID NO:3 is inserted together with the intron sequence of rice PLD gene, shown in SEQ ID NO:1.

EXAMPLES

The invention will now be described more concretely by way of examples thereof. It should be noted, however, the present invention is not restricted to the following examples.

Example 1

In the rice PLD gene, a first intron with a size of 173 bp exists at the region corresponding to the 5'-end non-coding region of the mRNA (SEQ ID NO: 1, WO 95/09234). The intron was checked for its influence on gene expression in plant cells. Primers of 20mer (5'-TCACCACCCGGTAAGCCCAG-3', (SEQ ID NO:4) 3'-CCCCCGCGTCCATCCCGCTC-5' (SEQ ID NO:5), each of which contains a region of 10 nucleotides originated from an exon, were synthesized and PCR was performed using rice genomic clone as a template. The PCR was performed using a mixture of 50 pmol each of the primers, 200 μM of dATP, dCTP, dGTP and dTTP, 1×PCR buffer (commercially available from TAKARA SHUZO) and 2.5 U of AmpliTaq DNA polymerase (TAKARA SHUZO), the total volume of the reaction mixture being 50 μl. The reaction was carried out according to the following thermal conditions and the cycle was repeated 30 times. That is, in a DNA THERMOCYCLER (commercially available from PARKIN ELMER CETUS), 94° C. for 1 minute, 40° C. for 1 minute and 72° C. for 2 minutes and 30 seconds.

The PCR product was subcloned into PCR II vector (commercially available from INVITROGEN) and a fragment was cut out with EcoRI. The fragment was blunted, and inserted into the SmaI site of pBI221 (a vector plasmid in which a β-glucuronidase gene (hereinafter referred to as "GUS") is inserted into a site downstream of a 35S promoter (hereinafter referred to as "35S pro")) commercially available from TOYOBO CO., LTD. to obtain a vector pBI221P (35S pro, PLD intron, GUS). This plasmid was digested with BamHI and the resulting fragments were blunted, followed by incorporation of the above-described fragment to construct a vector pBI221PP (35S pro, PLD intron×2, GUS).

The pIG221 (having the intron (SEQ ID NO:2) of catalase gene of castor-oil plant and GUS in the order mentioned, at a downstream region of 35S pro) described in Japanese Laid-open Patent Application (Kokai) No. 3-103182 was digested with XbaI and the resulting fragments were blunted, followed by insertion of the above-described PLD intron sequence to construct a vector pIG221P (35S pro, PLD intron, Catalase intron, GUS).

Rice cultured cells were prepared from immature embryo of Japonica rice variety Nihonbare (Hiei et al., The Plant Journal, 6, 271–282 (1994)), the above-described gene was introduced into the cells according to a reported method (Shimamoto et al. Nature, 338, 274–276 (1989)) and the β-glucuronidase activities (GUS) were measured. The results are shown in Table 1.

As shown in Table 1, by introducing two same or different introns, the GUS activity was prominently increased when compared with the cases where a single intron was used. Also it was proved that the DNA fragment having the nucleotide sequence of the PLD intron is the DNA fragment giving the gene expression-promoting effect when two or more of the DNA fragments are used.

TABLE 1

| Plasmid | GUS Activity |
|---|---|
| None | 7.2 |
| pBI221 (35S pro, GUS) | 14 |

TABLE 1-continued

| Plasmid | GUS Activity |
|---|---|
| pBI221P (35S pro, PLD intron, GUS) | 180 |
| pBI221PP (35S pro, PLD intron × 2, GUS) | 430 |
| pIG221 (35S pro, Catalase intron, GUS) | 160 |
| pIG221P (35S pro, PLD intron, Catalase intron, GUS) | 680 |

Example 2

The intron of maize ubiquitin gene (Ubi-1:Christensen A. H. et al. Plant Mol. Biol., 18, 675–689 (1982)) was also checked for the effect for promoting expression of foreign genes. Two kinds of vectors were used.

First, a vector for examining the effect of the intron when a single intron is inserted was constructed by the following method. That is, the region of the promoter and the intron of the ubiquitin gene was cut out with PstI and the obtained fragment (SEQ ID NO:3) was inserted into the PstI site of pUC18 vector. The intron region was cut out with BglII and BamHI and the obtained fragment was inserted into the BamHI site of pBI221 vector to obtain a vector pBI221U (35S pro, Ubiquitin intron, GUS).

Next, a vector for examining the effect of the intron when a plurality of introns are inserted was constructed by the following method. That is, the intron region was cut out with BglII and BamHI and the obtained fragment was blunted, followed by insertion of the resulting fragment to the SmaI site of the pBI221 vector. The BamHI site of this vector was blunted and the above-described PLD intron was inserted thereinto to obtain a vector pBI221PU (35S pro, PLD intron, Ubiquitin intron, GUS). The vectors were introduced into the protoplasts by the above-mentioned method and the GUS activities were measured.

As shown in Table 2, promotion of GUS expression was observed when a single ubiquitin intron was used. A stronger promotion effect was observed by employing both the PLD intron and the ubiquitin intron, than in cases where each of the introns was used individually.

TABLE 2

| Plasmid | GUS Activity (pmol MU/min./mg protein) |
|---|---|
| None | 3.3 |
| pBI221 (35S pro, GUS) | 13 |
| pBI221 (35S pro, PLD intron, GUS) | 100 |
| pBI221 (35S pro, Ubiquitin intron, GUS) | 360 |
| pBI221 (35S pro, PLD intron, Ubiquitin intron, GUS) | 780 |

What is claimed is:

1. A method for expressing a foreign gene comprising:
    inserting said foreign gene into a site downstream of a promoter; and
    expressing said foreign gene in a cell, wherein a plurality of intron-originated DNA fragments selected from the group consisting of SEQ ID NO:1, SEQ ID NO:2, SEQ ID NO:3, a variant having not less than 90% homology to SEQ ID NO:1, a variant having not less than 90% homology to SEQ ID NO:2, and a variant having not less than 90% homology to SEQ ID NO:3, which are the same or different and promote expression of foreign genes, are inserted into one or more sites upstream of said foreign gene; and wherein the level of expression of said foreign gene is higher than when only one of said intron-originated DNA fragments is inserted into a site upstream of said foreign gene.

2. The method according to claim 1, wherein said plurality of intron-originated DNA fragments are inserted into one or more sites between said promoter and said foreign gene.

3. The method according to claim 1 or 2, wherein said cell is a plant cell.

4. The method of claim 1, wherein at least one of said plurality of intron-originated DNA fragments consists of the sequence shown in SEQ ID NO;1 or a functional variant thereof having not less than 90% homology to SEQ ID NO:1.

5. The method according to claim 4, wherein said plurality of intron-originated DNA fragments comprises at least two copies consisting of the sequence shown in SEQ ID NO:1 or a functional variant thereof having not less than 90% homology to SEQ ID No:1.

6. The method according to claim 1, wherein at least one of said plurality of intron-originated DNA fragments consists of the sequence shown in SEQ ID No:2 or a functional variant thereof having not less than 90% homology to SEQ ID NO:2.

7. The method according to claim 6, wherein said plurality of intron-originated DNA fragments consists of the sequence shown in SEQ ID NO:1 or a functional variant thereof having not less than 90% homology to SEQ ID NO:1 and the sequence shown in SEQ ID NO:2 or a functional variant thereof having not less than 90% homology to SEQ ID NO:2.

8. The method according to claim 1, wherein at least one of said plurality of intron-originated DNA fragments consists of the sequence shown in SEQ ID NC:3 or a functional variant thereof having not less than 90% homology to SEQ ID NO:3.

9. The method according to claim 8, wherein said plurality of intron-originated fragments consists of the sequence shown in SEQ ID NO:1 or a functional variant thereof having not less than 90% homology to SEQ ID NO:1 and the sequence shown in SEQ ID NO:3 or a functional variant thereof having not less than 90% homology to SEQ ID NO:3.

10. A recombinant vector comprising:

a promoter;

a foreign gene inserted into a site downstream of said promoter; and a plurality of intron-originated DNA fragments which are the same or different and which promote expression of foreign genes, which are inserted into one or more sites upstream of said foreign gene, wherein said intron-originated DNA fragments consists of a sequence selected from the group consisting of SEQ ID NO:1, SEQ ID NO:2, SEQ ID NO:3 and a sequence having not less than 90% homology to one of SEQ ID NO:1, SEQ ID NO:2 or SEQ ID NO:3.

11. The recombinant vector according to claim 10, wherein said plurality of intron-originated DNA fragments are inserted into one or more sites between said promoter and said foreign gene.

12. The recombinant vector according to claim 10 or 11, which are replicable in a plant cell.

13. The recombinant vector according to claim 10, wherein at least one of said plurality of intron-originated DNA fragments consists of the sequence shown in SEQ ID NO;1 or a functional variant thereof having not less than 90% homology to SEQ ID NO:1.

14. The recombinant vector according to claim 13, wherein said plurality of intron-originated DNA fragments comprises at least two copies consisting of the sequence shown in SEQ ID NO:1 or a functional variant thereof having not less than 90% homology to SEQ ID NO:1.

15. The recombinant vector according to claim 10, wherein at least one of said plurality of intron-originated DNA fragments consists of the sequence shown in SEQ ID NO:2 or a functional variant thereof having not less than 90% homology to SEQ ID NO:2.

16. The recombinant vector according to claim 15, wherein said plurality of intron-originated DNA fragments consists of the sequence shown in SEQ ID NO:1 or a functional variant thereof having not less than 90% homology to SEQ ID NO:1 and the sequence shown in SEQ ID NO:2 or a functional variant thereof having not less than 90% homology to SEQ ID NO:2.

17. The recombinant vector according to claim 10, wherein at least one of said plurality of intron-originated DNA fragments consists of the sequence shown in SEQ ID NO:3 or a functional variant thereof having not less than 90% homology to SEQ ID NO;3.

18. The recombinant vector according to claim 17, wherein said plurality of intron-originated DNA fragments consists of the sequence shown in SEQ ID NO:1 or a functional variant thereof having not less than 90% homology to SEQ ID NO:1 and the sequence shown in SEQ ID NO:3 or a functional variant thereof having not less than 90% homology to SEQ ID NO:3.

19. A method for expressing a foreign gene, comprising:

inserting said foreign gene into a site downstream of a promoter; and expressing said foreign gene in a cell, characterized in that the sequence shown in SEQ ID NO:3 or a functional variant thereof having not less than 90% homology to SEQ ID NO:3 is inserted into a site upstream of said foreign gene, and said foreign gene is expressed.

20. A method for expressing a foreign gene, comprising:

inserting said foreign gene into a site downstream of a promoter; and expressing said foreign gene in a cell, wherein the sequence shown in SEQ ID NO:3 is inserted into a site upstream of said foreign gene, and said foreign gene is expressed.

21. The method according to claim 19, wherein the sequence shown in SEQ ID NO:3 or a functional variant thereof having not less than 90% homology to SEQ ID NO:3 is inserted between said promoter and said foreign gene.

22. The method according to claim 19, wherein said cell is a plant cell.

23. The method of claim 20, wherein said sequence shown in SEQ ID NO:3 is inserted between said promoter and said foreign gene.

24. The recombinant vector according to claim 10, wherein said at least one of said plurality of intron-originated DNA fragments consists of a sequence selected from the group consisting of SEQ ID NO:1, SEQ ID NO:2, SEQ ID NO:3.

25. A recombinant vector comprising:

a promoter;

a foreign gene inserted into a site downstream of said promoter; and a plurality of intron-originated DNA fragments which are the same or different and which promote expression of foreign genes, which are inserted into one or more sites upstream of said foreign gene, wherein each of said plurality of intron-originated DNA fragments consists of a sequence selected from the group consisting of SEQ ID NO:1, SEQ ID NO:2, and SEQ ID NO:3.

26. The recombinant vector according to claim 15, wherein said plurality of intron-originated DNA fragments consists of the sequence shown in SEQ ID NO:2 or a functional variant thereof having not less than 90% homology to SEQ ID NO:2 and the sequence shown in SEQ ID NO:3 or a functional variant thereof having not less than 90% homology to SEQ ID NO:3.

27. The recombinant vector according to claim 10, wherein expression of said foreign gene upon introduction of said vector into a host cell is higher than when only one of said intron-originated DNA fragments is inserted into a site upstream of said foreign gene.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 173 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Oryza sativa (xi) SEQUENCE DESCRIPTION: SEQ ID NO:1:

```
GTAAGCCCAG TGTGCTTAGG CTAAGCGCAC TAGAGCTTCT TGCTCGCTTG CTTCTTCTCC      60

GCTCAGATCT GCTTGCTTGC TTGCTTCGCT AGAACCCTAC TCTGTGCTGC GAGTGTCGCT     120

GCTTCGTCTT CCTTCCTCAA GTTCGATCTG ATTGTGTGTG TGGGGGGGCG CAG            173
```

(2) INFORMATION FOR SEQ ID NO:2:

(i) SEQUENCE CHARACTERISTICS:
        (A) LENGTH: 217 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Castor-oil plant (xi) SEQUENCE DESCRIPTION: SEQ ID NO:2:

```
ACATGGATCC CTACAGGGTA AATTTCTAGT TTTTCTCCTT CATTTTCTTG GTTAGGACCC      60

TTTTCTCTTT TTATTTTTTT GAGCTTTGAT CTTTCTTTAA ACTGATCTAT TTTTTAATTG     120

ATTGGTTATG GTGTAAATAT TACATAGCTT TAACTGATAA TCTGATTACT TTATTTCGTG     180

TGTCTATGAT GATGATGATA GTTACAGAAC CGTCGAC                              217
```

(2) INFORMATION FOR SEQ ID NO:3:

(i) SEQUENCE CHARACTERISTICS:
        (A) LENGTH: 1010 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Maize (xi) SEQUENCE DESCRIPTION: SEQ ID NO:3:

```
GTACGCCGCT CGTCCTCCCC CCCCCCCCCT CTCTACCTTC TCTAGATCGG CGTTCCGGTC      60

CATGGTTAGG GCCCGGTAGT TCTACTTCTG TTCATGTTTG TGTTAGATCC GTGTTTGTGT     120

TAGATCCGTG CTGCTAGCGT TCGTACACGG ATGCGACCTG TACGTCAGAC ACGTTCTGAT     180

TGCTAACTTG CCAGTGTTTC TCTTTGGGGA ATCCTGGGAT GGCTCTAGCC GTTCCGCAGA     240

CGGGATCGAT TCATGATTT TTTTTGTTTC GTTGCATAGG GTTTGGTTTG CCCTTTTCCT     300

TTATTTCAAT ATATGCCGTG CACTTGTTTG TCGGGTCATC TTTTCATGCT TTTTTTTGTC     360

TTGGTTGTGA TGATGTGGTC TGGTTGGGCG GTCGTTCTAG ATCGGAGTAG AATTCTGTTT     420

CAAACTACCT GGTGGATTTA TTAATTTTGG ATCTGTATGT GTGTGCCATA CATATTCATA     480
```

-continued

```
GTTACGAATT GAAGATGATG GATGGAAATA TCGATCTAGG ATAGGTATAC ATGTTGATGC        540

GGGTTTTACT GATGCATATA CAGAGATGCT TTTTGTTCGC TTGGTTGTGA TGATGTGGTG        600

TGGTTGGGCG GTCGTTCATT CGTTCTAGAT CGGAGTAGAA TACTGTTTCA AACTACCTGG        660

TGTATTTATT AATTTTGGAA CTGTATGTGT GTGTCATACA TCTTCATAGT TACGAGTTTA        720

AGATGGATGG AAATATCGAT CTAGGATAGG TATACATGTT GATGTGGGTT TTACTGATGC        780

ATATACATGA TGGCATATGC AGCATCTATT CATATGCTCT AACCTTGAGT ACCTATCTAT        840

TATAATAAAC AAGTATGTTT TATAATTATT TTGATCTTGA TATACTTGGA TGATGGCATA        900

TGCAGCAGCT ATATGTGGAT TTTTTTAGCC CTGCCTTCAT ACGCTATTTA TTTGCTTGGT        960

ACTGTTTCTT TTGTCGATGC TCACCCTGTT GTTTGGTGTT ACTTCTGCAG                  1010

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:4:

TCACCACCCG GTAAGCCCAG                                                    20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:5:

CTCGCCCTAC CTGCGCCCCC                                                    20
```